United States Patent
Sampson-Johannes et al.

(12)

(10) Patent No.: US 6,296,845 B1
(45) Date of Patent: Oct. 2, 2001

(54) SELECTIVE KILLING AND DIAGNOSIS OF P53+ NEOPLASTIC CELLS

(75) Inventors: Adam Sampson-Johannes, Berkeley; David Kirn, Mill Valley, both of CA (US)

(73) Assignee: Onyx Pharmaceuticals Inc., Richmond, CA (US)

( * ) Notice: Subject to any disclaimer, the term of this patent is extended or adjusted under 35 U.S.C. 154(b) by 0 days.

(21) Appl. No.: 09/190,930

(22) Filed: Nov. 12, 1998

Related U.S. Application Data (60) Provisional application No. 60/069,357, filed on Dec. 12, 1997.

(51) Int. Cl.[7] .................. A61K 48/00; C12N 15/861; C12N 15/63; C12Q 1/70
(52) U.S. Cl. .................. 424/93.2; 424/93.6; 435/69.1; 435/320.1; 435/325; 435/366; 435/5; 435/6; 435/7.1; 435/455; 435/456
(58) Field of Search .................. 435/69.1, 320.1, 435/235.1, 325, 366, 236, 5, 6, 7.1, 455, 456; 424/93.2, 93.6

(56) References Cited

U.S. PATENT DOCUMENTS 5,677,178 * 10/1997 McCormick .................. 435/325

OTHER PUBLICATIONS

Kim et al., "Preferential replication of an E1B– attenuated adenovirus . . . " Brit.Jrnl. of Cancer, V. 78, No. 2 (1998) p. 150.

Heise et al., "ONYX–015, an E1B gene–attenuated adenovirus, causes . . . " Nature Med., V. 3, No. 6 (1997), pp. 639–645.

Heise et al., "Antitumor efficacy following intravenous administration . . . " Proc Annu Meeting AM Assoc. Cancer Res., V. 38, (1997) p. A66.

* cited by examiner

Primary Examiner—David Guzo
(74) Attorney, Agent, or Firm—Gregory Giotta (57) ABSTRACT

Methods and compositions for treating and diagnosing neoplastic disease using viruses are provided. Preferably, mutant adenovirus lacking viral proteins which bind and/or inactivate p53 are administered to a patient having a neoplasm which comprises cells exhibiting p53 and lacking, or substantially devoid of mismatch repair activity. The mutant virus is able to substantially produce a replication phenotype in such neoplastic cells but is substantially unable to produce a replication phenotype in non-replicating, non-neoplastic cells having essentially normal p53 function. The preferential generation of a replication phenotype in neoplastic cells results in a preferential killing of the neoplastic cells, either directly or by expression of a cytotoxic gene in cells expressing a viral replication phenotype.

12 Claims, 2 Drawing Sheets

SELECTIVE KILLING AND DIAGNOSIS OF P53+ NEOPLASTIC CELLS

This application claims priority from U.S. Provisional Application No. 60/069,357, filed Dec. 12, 1997.

TECHNICAL FIELD

This invention is in the field of cancer, and provides a description of viral therapy and diagnosis of neoplastic cells that exhibit p53 tumor suppressor activity but lack mismatch repair enzymatic activity.

BACKGROUND

The proliferation of normal cells is thought to be regulated by growth-promoting proto-oncogenes counterbalanced by growth-constraining tumor-suppressor genes. Mutations that potentiate the activities of proto-oncogenes create the oncogenes that force the growth of neoplastic cells. Conversely, genetic lesions that inactivate tumor suppressor genes, generally through mutation(s) that lead to a cell being homozygous for the inactivated tumor suppressor allele, can liberate the cell from the normal replicative constraints imposed by these genes. Usually, an inactivated tumor suppressor gene (e.g., p53, RB, DCC, NF-1) in combination with the formation of an activated oncogene (i.e., a proto-oncogene containing an activating structural or regulatory mutation) can yield a neoplastic cell capable of essentially unconstrained growth (i.e., a transformed cell).

Oncogenic transformation of cells leads to a number of changes in cellular metabolism, physiology, and morphology. One characteristic alteration of oncogenically transformed cells is a loss of responsiveness to constraints on cell proliferation and differentiation normally imposed by the appropriate expression of cell-growth regulatory genes.

While different types of genetic alterations may all lead to altered expression or function of cell-growth regulatory genes and to abnormal growth, it is generally believed that more than one event is required to lead to neoplastic transformation of a normal cell to a malignant one (Land et al. (1983) *Nature* 304: 596; Weinberg R A (1989) *Cancer Res.* 49: 3713). The precise molecular pathways and secondary changes leading to malignant transformation for most cell types are not clear. A number of cases have been reported in which altered expression or activity of some proteins with putative cell-cycle control functions and/or implicated in the formation of functional transcriptional complexes, such as p53 and RB, can lead to loss of proliferation control in cells (Ullrich et al. (1992) *J. Biol. Chem.* 267: 15259; Hollstein et al. (1991) *Science* 253: 49; Sager R (1992) *Curr. Opin. Cell. Biol.* 4: 155: Levine et al. (1991) *Nature* 351: 453).

Some oncogenes have been found to possess characteristic activating mutations in a significant fraction of certain cancers. For example, particular mutations in the $ras^H$ and $ras^K$ coding regions (e.g., codon 12, codon 61; Parada et al. (1984) *Nature* 312: 649) are associated with oncogenic transformation of cultured cells and are present in a striking percentage of specific human cancers (e.g., colon adenocarcinoma, bladder carcinoma, lung carcinoma and adenocarcinoma, hepatocarcinoma). These findings have led to the development of diagnostic and therapeutic reagents (e.g., polynucleotide probes and antibodies) that specifically recognize the activated form(s) of such oncogenes (U.S. Pat. No. 4,798,787 and U.S. Pat. No. 4,762,706).

The excessive or inappropriate expression of other oncogenes, such as myc, erbB-2, and pim-1, appears to be able to potentiate oncogenic transformation without necessarily requiring the presence of activating mutation(s) in the coding region. Overexpression of erbB-2 is frequently found in adenocarcinoma of the breast, stomach, and ovary, and erbB-2 levels in these cell types might serve as a diagnostic marker for neoplasia and/or may correlate with a specific tumor phenotype (e.g., resistance to specific drugs, growth rate, differentiation state).

Transgenic animals harboring various oncogenes (U.S. Pat. No. 4,736,866 and U.S. Pat. No. 5,087,571) or functionally disrupted tumor suppressor genes (Donehower et al. (1992) *Nature* 356: 215) have been described for use in carcinogen screening assays, among other potential uses.

Despite this progress in developing a more defined model of the molecular mechanisms underlying the transformed phenotype and neoplasia, few significant therapeutic methods applicable to treating cancer beyond conventional chemotherapy have resulted. Many conventional chemotherapeutic agents have a low therapeutic index, with therapeutic dosage levels being at or near dosage levels which produce toxicity. Toxic side effects of most conventional chemotherapeutic agents are unpleasant and lead to life-threatening bone marrow suppression, among other side effects.

Recent approaches for performing gene therapy to correct or supplement defective alleles which cause congenital diseases, such as cystic fibrosis, have been attempted with reports of limited initial success. Some gene therapy approaches involve transducing a polynucleotide sequence capable of expressing a functional copy of a defective allele into a cell in vivo using replication-deficient recombinant adenovirus (Rosenfeld et al. (1992) *Cell* 68: 143). Some of these gene therapy methods are efficient at transducing polynucleotides into isolated cells explanted from a patient, but have not been shown to be highly efficient in vivo. Therapeutic approaches to cancer which rely on transfection of explanted tumor cells with polynucleotides encoding tumor necrosis factor (TNF) and interleukin-2 (IL-2) have been described (Pardoll D (1992) *Curr. Opin. Oncol.* 4: 1124).

Although it might someday prove possible for gene therapy methods to be adapted to correct defective alleles of oncogenes or tumor suppressor genes in transformed cells in vivo, present gene therapy methods have not been reported to be able to efficiently transduce and correctly target (e.g., by homologous recombination) a sufficient percentage of neoplastic cells for practical gene therapy of neoplasia in situ. The nature of cancer biology mandates that a substantial fraction of the neoplastic cells, preferably all of the clonal progeny of the transformed cell, are ablated for an effective therapeutic effect. Moreover, present methods for gene therapy are very expensive, requiring ex vivo culturing of explanted cells prior to reintroduction into a patient. Widespread application of such methods, even if they were effective, would be prohibitively expensive.

Thus, there exists a need in the art for methods and compositions for diagnosis and therapy of neoplastic diseases, especially for methods which selectively ablate neoplastic cells without the undesirable killing of non-neoplastic cells that is typical of conventional antineoplastic chemotherapy.

In this regard it is particularly noteworthy that investigators have recently reported the selective killing of neoplastic cells that lack the tumor suppressor p53 with a mutant adenovirus. See, U.S. Pat. No. 5,677,178, and Bischoff, J. R., et al., *Science*, vol. 274, pages 373–376 (1996). The selective killing is provided by exploiting the differential ability of the mutant adenovirus to replicate in and lyse neoplastic cells, but not non-neoplastic cells. More specifically, it was shown that certain replication-deficient recombinant adenoviruses, particularly those defective in E1b function (E1b-), can exhibit a replication phenotype in neoplastic cells lacking p53 tumor suppressor function, and effectively kill these cells. It was also shown that non-neoplastic cells containing normal p53 function are relatively resistant to killing by the replication-deficient recombinant adenovirus.

It has now been shown that there is a population of neoplastic cells that exhibit p53, and that are also killed by mutant E1b-adenovirus. Heise, C., et al. Nature Medicine, vol. 3, pages 639–645 (1997). The genetic predisposition which facilitates E1b-killing in these neoplastic cells is not known. It would thus be particularly beneficial to a physician who would prescribe treatment for a cancer patient to have a method of determining if a patient's tumor consist of p53+ cells that are susceptible to killing by mutant E1b-adenovirus.

The references discussed herein are provided solely for their disclosure prior to the filing date of the present application. Nothing herein is to be construed as an admission that the inventors are not entitled to antedate such disclosure by virtue of prior invention.

SUMMARY OF THE INVENTION

The present invention provides novel methods and compositions using recombinant replication deficient adenovirus lacking an expressed viral oncoprotein capable of binding a functional p53 tumor suppressor gene product for diagnosing and/or ablating neoplastic cells that exhibit the tumor suppressor p53, while having little or no effect on non-neoplastic cells. In a manner not understood, the neoplastic cells show reduced p53 function by the lack of, or substantial reduction in mismatch repair activity as assessed by the ability of these cells to support viral replication. The difference in replication phenotype of the adenovirus constructs of the invention in neoplastic and non-neoplastic cells provides a biological basis for viral-based therapy of cancer. Expression of adenoviral cytopathic effects are correlated with the adenoviral replication phenotype characteristic of neoplastic cells infected with the recombinant adenovirus constructs of the invention, thus discriminating between neoplastic and non-neoplastic cells and providing selective cytotoxicity of neoplastic cells. Although the methods are described in detail specifically for adenoviral constructs, the methods are believed to be applicable to essentially any virus type wherein efficient replication requires binding and/or sequestration and/or inactivation of a host cell protein that is present in non-neoplastic cells but is substantially absent or nonfunctional in neoplastic cells (e.g., p53).

In order for adenovirus to replicate efficiently in cells, the adenoviral E1b gene product, p55, forms a complex with the host cell p53 protein, thereby sequestering and/or inactivating p53 and producing a cell that is deficient in p53 function. The latter also occurs in p53+ cells that lack or are substantially devoid of mismatch repair activity. Such a cell made deficient in p53 function could support replication of the adenovirus. In this way, wild-type adenovirus is able to replicate in cells containing p53, as the adenovirus p55 proteins inactivates and/or sequesters the host cell p53 protein.

As mentioned above, the lack of, or loss of mismatch repair activity effectively causes a neoplastic cell that is p53 positive to be non-functional for p53 mediated abrogation of viral replication. Such cells are thus susceptible to killing by the invention viruses.

In one embodiment of the invention, a recombinant adenovirus comprising an E1b locus encoding a mutant p55 protein that is substantially incapable of forming a functional complex with p53 protein in infected cells is administered to an individual or cell population comprising a neoplastic cell capable of being infected by the recombinant adenovirus. The substantial incapacity of the recombinant adenovirus to effectively sequester p53 protein in infected non-neoplastic cells results in the introduced recombinant adenoviral polynucleotide(s) failing to express a replication phenotype in non-neoplastic cells. By contrast, neoplastic cells which lack a functional p53 protein support expression of a replication phenotype by the introduced recombinant adenovirus which leads to ablation of the neoplastic cell by an adenoviral cytopathic effect and/or expression of a negative selection gene linked to the replication phenotype. In preferred variations of these embodiments, the recombinant adenovirus comprises an E1b locus encoding a mutant p55 which is substantially incapable of binding p53 and may optionally also lack a functional p19 protein (i.e., incapable of inhibiting expression of adenoviral early region genes in the presence of E1a polypeptides). Recombinant adenoviruses of the invention may further comprise a mutant p19 gene which produces enhanced cytopathic effects; such a mutant known in the art is the p19 cyt mutant gene. However, it may be preferable to retain functional p19 in some mutants to maintain the integrity of viral DNA during the infection.

The invention provides recombinant adenovirus constructs which are replication defective in non-neoplastic cells but capable of expressing a replication phenotype in neoplastic cells lacking functional p53. The novel recombinant adenovirus constructs comprise a mutation, such as a deletion or point mutation, in the E1b gene regions, especially in the sequences encoding the E1b p55 protein.

The invention also provides recombinant papovaviruses, such as human papillomavirus (HPV), polyomaviruses (e.g., BK, JC) and SV40, which lack functional proteins for binding and/or inactivating p53. Human papillomavirus mutants lacking expression of functional E6 protein will substantially lack the capacity to effectively degrade p53 and thus will be capable of manifesting a replication phenotype in $p53^{(-)}$ cells but not in cells containing a sufficient level of functional p53.

The invention also provides novel methods for treating a neoplastic disease comprising the steps of administering to a patient a recombinant virus capable of preferentially expressing a replication phenotype and/or expressing a cytopathic effect in a neoplastic cell population as compared to expression in a non-neoplastic cell population.

DEFINITIONS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. As used herein, the term "recombinant" indicates that a polynucleotide construct (e.g., and adenovirus genome) has been generated, in part, by intentional modification by man.

As used herein, the term "replication deficient virus" refers to a virus that preferentially inhibits cell proliferation or induces apoptosis in a predetermined cell population (e.g., cells substantially lacking p53) which supports expression of a virus replication phenotype, and which is substantially unable to inhibit cell proliferation, induce apoptosis, or express a replication phenotype in cells comprising normal p53 levels characteristic of non-replicating, non-transformed cells. Typically, a replication deficient virus exhibits a substantial decrease in plaquing efficiency on cells comprising normal p53 function.

As used herein, mismatch repair activity (MMR) refers to a system of proteins that are involved in recognizing and repairing base pair mismatches and single strand insertion/deletion loops (ILPs) arising in the genome by various mechanisms during the replication, recombination, or chemical modification of DNA.

The loss of MMR activity can occur through a number of mechanisms including loss of the chromosomes that the genes are on that encode the proteins, mutations in the genes, degradation of the enzyme(s) involved and so on.

As used herein, the term "p53 function" refers to the property of having an essentially normal level of a polypeptide encoded by the p53 gene (i.e., relative to non-neoplastic cells of the same histological type), wherein the p53 polypeptide is capable of binding an E1b p55 protein of wild-type adenovirus 2 or 5. For example, p53 function may be lost by production of an inactive (i.e., mutant) form of p53 or by a substantial decrease or total loss of expression of p53 polypeptide(s). Also, p53 function may be substantially absent in neoplastic cells which comprise p53 alleles encoding wild-type p53 protein; for example, a genetic alteration outside of the p53 locus, such as a mutation that results in aberrant subcellular processing or localization of p53 (e.g., a mutation resulting in localization of p53 predominantly in the cytoplasm rather than the nucleus) can result in a loss of p53 function.

In certain instances when a neoplastic cell exhibits wild-type p53 protein, and the cell is ablated by viruses of the instant invention, this can be caused by alterations in cellular constituents that affect, or are necessary for the expression of partial or all of the activities associated with p53. A key aspect of the instant invention is the realization that one way that this can occur, for example, is when neoplastic cells are deficient in, or lack, mismatch repair (MMR) enzymatic activity. See, Anthoney, D. A., et al. Cancer Research, vol. 56, pages 1374–1381, (1996): and Drummond, J. T., et al. Journal of Biological Chemistry, vol. 271, pages 19645–19648 (1996). Thus, it would be expected that certain neoplastic cells will exhibit normal wild-type p53 function, yet support adenovirus replication when the virus lacks E1b p55 because the cell lacks, or is substantially devoid of mismatch repair activity. Indeed, it has been suggested that the mismatch repair, and p53 pathways are biochemically linked. See, Drummond, J. T., et al. Journal of Biological Chemistry, vol. 271, pages 19645–19648 (1996).

As used herein, the term "replication phenotype" refers to one or more of the following phenotypic characteristics of cells infected with a virus such as a replication deficient adenovirus: (1) substantial expression of late gene products, such as capsid proteins (e.g., adenoviral penton base polypeptide) or RNA transcripts initiated from viral late gene promoter(s), (2) replication of viral genomes or formation of replicative intermediates, (3) assembly of viral capsids or packaged virion particles, (4) appearance of cytopathic effect (CPE) in the infected cell, (5) completion of a viral lytic cycle, and (6) other phenotypic alterations which are typically contingent upon abrogation of p53 in non-neoplastic cells infected with a wild-type replication competent DNA virus encoding functional oncoprotein(s). A replication phenotype comprises at least one of the listed phenotypic characteristics, preferably more than one of the phenotypic characteristics.

The term "antineoplastic replication deficient virus" is used herein to refer to a recombinant virus which has the functional property of inhibiting development or progression of a neoplasm in a human, by preferential cell killing of infected neoplastic cells relative to infected non-replicating, non-neoplastic cells of the same histological cell type.

As used herein, "neoplastic cells" and "neoplasia" refer to cells which exhibit relatively autonomous growth, so that they exhibit an aberrant growth phenotype characterized by a significant loss of control of cell proliferation. Neoplastic cells comprise cells which may be actively replicating or in a temporary non-replicative resting state ($G_1$ or $G_0$); similarly, neoplastic cells may comprise cells which have a well-differentiated phenotype, a poorly-differentiated phenotype, or a mixture of both type of cells. Thus, not all neoplastic cells are necessarily replicating cells at a given timepoint. The set defined as neoplastic cells consists of cells in benign neoplasms and cells in malignant (or frank) neoplasms. Frankly neoplastic cells are frequently referred to as cancer, typically termed carcinoma if originating from cells of endodermal or ectodermal histological origin, or sarcoma if originating from cell types derived from mesoderm.

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

As used herein, "physiological conditions" refers to an aqueous environment having an ionic strength, pH, and temperature substantially similar to conditions in an intact mammalian cell or in a tissue space or organ of a living mammal. Typically, physiological conditions comprise an aqueous solution having about 150 mM NaCl (or optionally KCl), pH 6.5–8.1, and a temperature of approximately 20–45° C. Generally, physiological conditions are suitable binding conditions for intermolecular association of biological macromolecules. For example, physiological conditions of 150 mM NaCl, pH 7.4, at 37° C. are generally suitable.

DETAILED DESCRIPTION

All reference to scientific or patent literature in the following discussion is intended to indicate incorporation of such reference in its entirety, whether or not there is an explicit statement to that effect.

Generally, the nomenclature used hereafter and the laboratory procedures in cell culture, molecular genetics, and molecular virology described below are those well known and commonly employed in the art. Standard techniques are used for recombinant nucleic acid methods, polynucleotide synthesis, polypeptide synthesis, generation and propagation of virus stocks (including cell lines capable of trans-complementation of replication deficient virus stocks), cell culture, and the like. Generally enzymatic reactions and purification steps are performed according to the manufacturer's specifications. The techniques and procedures are generally performed according to conventional methods in the art and various general references (see, generally, Sambrook et al. Molecular Cloning: A Laboratory Manual, 2d ed. (1989) Cold Spring Harbor Laboratory Press, Cold Spring Harbor, N.Y.; *Virology*, Second edition, eds. Fields B N and Knipe D M, (1990) Raven Press, New York, N.Y., incorporated herein by reference) which are provided throughout this document. The procedures therein are believed to be well known in the art and are provided for the convenience of the reader. All the information contained therein is incorporated herein by reference.

Neoplasia is a pathological condition which is characterized, in part, by the generation of neoplastic cells having variant genotypes and phenotypes. Some tumor cells may lack p53 function; such cells are designated $p53^{(-)}$. Also, there may be neoplastic cells which comprise essentially normal levels of p53(p53+); such cells having normal p53 may lack other oncoproteins (e.g., tumor suppressor gene products other than p53 i.e. RB) which can provide the basis for antineoplastic viral constructs which can preferentially manifest a replication phenotype in such neoplastic cells.

A basis of the present invention is that several DNA viruses which infect mammalian cells (e.g., adenoviruses; papovaviruses such as BK and JC, SV40, and papillomaviruses such as HPV, and the like) encode viral proteins which are essential for efficient progression through the viral replication cycle; some of these viral proteins sequester cellular proteins, such as those involved in cell-cycle control and/or formation of transcription complexes, as a necessary condition for efficient viral replication. In the absence of the viral proteins which bind, sequester, or degrade p53, viral replication is substantially inhibited. Normal (i.e., non-neoplastic) cells which are infected with a mutant virus lacking the ability to sequester or degrade p53 are generally unable to support replication of the mutant virus, hence such mutant viruses are considered to be replication deficient (or replication defective). However, since the sequestration or degradation of p53 is not necessary for viral replication in cells which lack functional p53 (such cells are designated $p53^{(-)}$) it is possible that replication deficient mutant viruses which are defective for p53 sequestration or degradation may express a replication phenotype in such $p53^{(-)}$ cells to a greater extent than in cells having essentially normal p53 function. Neoplastic cells frequently lack p53 function (a $p53^{(-)}$ cell). Hence, some replication deficient viral mutants may preferentially exhibit a replication phenotype in neoplastic cells.

Viral mutants lacking the capacity to express a functional p53 inactivating protein (e.g., adenovirus E1b p55, HPV E6 protein) will manifest a replication phenotype in $p53^{(-)}$ cell. Cytotoxicity linked to the expression of a replicative phenotype can therefore be used as a basis for preferentially killing neoplastic cells having a $p53^{(-)}$ phenotype. Although some replicating non-neoplastic cells may transiently exhibit a $p53^{(-)}$ phenotype during progression through the cell cycle, the viral mutants of the invention may be used for preferential, albeit not necessarily completely selective, killing of neoplastic cells, thus constituting a useful antineoplastic therapy modality to be used alone or in combination with other modalities of treatment.

Although the methods and compositions presented below are described specifically for methods relating to replication deficient adenoviral constructs, it is believed that the invention can be practiced with other DNA viruses encoding oncoproteins which sequester or enhance the degradation of p53 protein, for example replication deficient papillomavirus species (e.g., mutants of HPV types 16, 18, 33) that contain mutations in the E6 which substantially abrogate p53. In addition to members of the family Adenoviridae (specifically the genus Mastadenovirus), it is believed that members of the family Papovaviridae, especially papillomavirus and polyomavirus, which encode viral proteins that sequester and/or inactivate p53 are suitable for use in the methods of the invention.

For a general description of adenovirus and papovavirus biology, *Virology*, Second edition, eds. Fields B N and Knipe D M, Vol.2, pp. 1651–1740, Raven Press, New York, N.Y., incorporated herein by reference, may be referred to for guidance. The following specific descriptions refer to, but are not limited to, adenovirus serotype 5 and adenovirus serotype 2. Adenovirus type 2 provides a convenient reference for the numbering convention of the E1b viral gene region, and other viral gene regions. It is believed that those of skill in the art will readily identify the corresponding positions in other adenoviral serotypes. References to human papillomavirus generally refer to a type associated with neoplasia (e.g., types 16, 18, or 33), although non-oncogenic types may also be used.

E1b Mutants

A function of the cellular phosphoprotein p53 is to inhibit the progression of mammalian cells through the cell cycle. Wild-type adenovirus E1b p55 protein binds to p53 in infected cells that have p53 and produce a substantial inactivation of p53 function, likely by sequestering p53 in an inactive form. Functional E1b p55 protein is essential for efficient adenoviral replication in cells containing functional p53. Hence, adenovirus variants which substantially lack the ability to bind p53 are replication deficient in non-replicating, non-neoplastic cells having normal levels of functional p53.

Human tumor cells frequently are homozygous or heterozygous for mutated (e.g., substitution, deletion, frameshift mutants) p53 alleles, and lack p53 function necessary for normal control of the cell cycle (Hollstein et al. (1991) *Science*253: 49; Levine et al. (1991) op.cit., incorporated herein by reference). Thus, many neoplastic cells are $p53^{(-)}$, either because they lack sufficient levels of p53 protein and/or because they express mutant forms of p53 which are incapable of substantial p53 function, and which may substantially diminish p53 function even when wild-type p53 may be present (e.g., by inhibiting formation of functional multimers). Some neoplastic cells may comprise alleles encoding essentially wild-type p53 proteins, but may comprise a second site mutation that substantially abrogates p53 function, such as a mutation that results in p53 protein being localized in the cytoplasm rather than in the nucleus; such second site mutants also substantially lack p53 function.

It is believed that replication deficient adenovirus species which lack the capacity to complex p53 but substantially retain other essential viral replicative functions will exhibit a replication phenotype in cells which are deficient in p53 function (e.g., cells which are homozygous for substantially deleted p53 alleles, cells which comprise mutant p53 proteins which are essentially nonfunctional cells that exhibit wild-type p53 but that are deficient in, or lack, mismatch repair (MMR) activity) but will not substantially exhibit a replicative phenotype in non-replicating, non-neoplastic cells. Such replication deficient adenovirus species are referred to herein for convenience as E1b-p53$^{(-)}$ replication deficient adenoviruses.

A cell population (such as a mixed cell culture or a human cancer patient) which comprises a subpopulation of neoplastic cells lacking p53 function and a subpopulation of non-neoplastic cells which express essentially normal p53 function can be contacted under infective conditions (i.e., conditions suitable for adenoviral infection of the cell population, typically physiological conditions) with a composition comprising an infectious dosage of a E1b-p53$^{(-)}$ replication deficient adenovirus. Such contacting results in infection of the cell population with the E1b-p53$^{(-)}$ replication deficient adenovirus. The infection produces preferential expression of a replication phenotype in a significant fraction of the cells comprising the subpopulation of neoplastic cells lacking p53 function but does not produce a substantial expression of a replicative phenotype in the subpopulation of non-neoplastic cells having essentially normal p53 function. The expression of a replication phenotype in an infected p53$^{(-)}$ cell results in the death of the cell, such as by cytopathic effect (CPE), cell lysis, apoptosis, and the like, resulting in a selective ablation of neoplastic p53$^{(-)}$ cells from the cell population.

Typically, E1b-p53$^{(-)}$ replication deficient adenovirus constructs suitable for selective killing of p53(–) neoplastic cells comprise mutations (e.g., deletions, substitutions, frameshifts) which inactivate the ability of the E1b p55 polypeptide to bind p53 protein effectively. Such inactivating mutations typically occur in the regions of p55 which bind p53. Optionally, the mutant E1b region may encode and express a functional p19 protein encoded by the E1b region remains and that is functional in transactivation of adenoviral early genes in the absence of E1a polypeptides.

Suitable E1b-p53$^{(-)}$ replication deficient adenovirus constructs for use in the methods and compositions of the invention include, but are not limited to the following examples: (1) adenovirus type 2 dl 1520, which contains a C to T mutation at nucleotide position 2022 that generates a stop codon 3 amino acids downstream of the AUG codon used for initiation of translation of the p55 protein and a deletion between nucleotides 2496 and 3323 replaced with a small linker insertion that generates a second stop codon at nucleotide 3336; the expression of the p19 protein is essentially unaffected (Barker and Berk (1987) *Virology* 156: 107, incorporated herein by reference, and (2) a composite adenovirus construct comprising adenovirus type 2 dl 1520 comprising at least the position 2022 mutation and/or the 2496–3323 deletion mutation, or a substantial portion thereof, and an additional mutation in p19 to yield a p19 cyt mutant; the composite virus construct lacks p55 and comprises the enhanced cytopathic effect of the p19 cyt mutation. Ad2 dl 1520 are available from Dr. A. Berk, University of California at Los Angeles, Los Angeles, Calif., and are described in the literature, including Barker and Berk (1987) *Virology* 56: 107, incorporated herein by reference.

It may be preferable to incorporate additional mutations into such adenovirus constructs to inhibit formation of infectious virions in neoplastic cells which otherwise would support replication of the E1b-p53$^{(-)}$ mutants. Such additional inactivating mutations would be preferred in therapeutic modalities wherein complete viral replication forming infectious virions capable of spreading to and infecting adjacent cells is undesirable. These fully inactivated mutants are referred to as nonreplicable E1b-p53$^{(-)}$ mutants. Such nonreplicable mutants comprise mutations which prevent formation of infectious virions even in p53$^{(-)}$RB$^{(-)}$ cells; such mutations typically are structural mutations in an essential virion protein or protease.

However, in many modalities it is desirable for the mutant virus to be replicable and to form infectious virions containing the mutant viral genome which may spread and infect other cells, thus amplifying the antineoplastic action of an initial dosage of mutant virus.

Additional E1b$^{(-)}$ mutants lacking the capacity to bind p53 can be generated by those of skill in the art by generating mutations in the E1b gene region encoding the p55 polypeptide, expressing mutant p55 polypeptides, contacting the mutant p55 polypeptides with p53 or a binding fragment of p53 under aqueous binding conditions, and identifying mutant E1b polypeptides which do not specifically bind p53 as being candidate E1b$^{(-)}$ mutants suitable for use in the invention.

More typically, a functional assay will be used to identify candidate E1b$^{(-)}$ mutants. For example, the Friend assay for determination of p53 function will be performed essentially as described in Frebourg et al. (1992) *Cancer Res.* 52: 6977, incorporated herein by reference. E1b mutants which lack the capacity to inactivate p53 will be identified as candidate E1b$^{(-)}$ replication deficient mutants.

A large number of adenovirus that are mutant in E1b can be employed in the instant invention. Several are described in U.S. patent application Ser. No. 60/034616, filed Dec. 31, 1996.

E1a/E1b Double Mutants

The loss of retinoblastoma tumor suppressor gene (RB) gene function has been associated with the etiology of various types of tumors. Some human tumor cells lack both p53 function and RB function, either by mutational inactivation or deletion of one or both protein species. Such cells are termed p53$^{(-)}$RB$^{(-)}$ cells.

It is believed that replication deficient adenovirus species which lack the capacity to bind p53 and which also lack the capacity to bind RB, but which substantially retain other essential viral replicative functions will preferentially exhibit a replication phenotype in p53$^{(-)}$RB$^{(-)}$ cells. A replication phenotype will also be exhibited in tumor cells that are p53+ but lack, or are deficient in mismatch repair activity. Such replication deficient adenovirus species are referred to herein for convenience as E1a-RB$^{(-)}$/E1b-p53$^{(-)}$ replication deficient adenoviruses, or simply E1a/E1b double mutants. Such E1a/E1b double mutants can be constructed as described in U.S. Pat. No. 5,677,178, incorporated herein by reference.

Negative Selection Viral Constructs

Although expression of an adenoviral replication phenotype in an infected cell correlates with viral-induced cytotoxicity, generally by cell lysis, cytopathic effect (CPE), apoptosis, or other mechanisms of cell death, it may often be preferable to augment the cytotoxicity of a recombinant adenovirus that is to be used for antineoplastic therapy. Such augmentation may take the form of including a negative selection gene in the recombinant adenovirus, typically operably linked to an adenoviral promoter which exhibits positive transcriptional modulation in cells expressing a replication phenotype. See, U.S. Pat. No. 5,677,178. For example, a HSV tk gene cassette may be operably linked immediately downstream of an E3 promoter of a replication deficient adenovirus. Frequently, it is desirable to delete a nonessential portion (i.e., for viral replication and packaging) of the adenoviral genome to accommodate the negative selection cassette; thus a substantial portion of the E3 gene region may be deleted and replaced with a negative selection cassette such as an HSV tk gene operably linked to an E2 promoter (and enhancer) or other suitable promoter/enhancer. Alternatively, a negative selection gene may be operably linked to an adenovirus late region promoter to afford efficient expression of the negative selection gene product in cells expressing a replication phenotype characterized by transcription from late gene promoters.

Expression of the HSV tk gene in a cell is not directly toxic to the cell, unless the cell is exposed to a negative selection agent such as gancyclovir or FIAU. Infected cells expressing a replication phenotype wherein a negative selection gene is substantially expressed may produce essentially no additional cytotoxicity until the negative selection agent (e.g., gancyclovir) is administered in an effective selective dosage, at which time the infected cells expressing the tk gene will be selectively ablated; thus negative selection can be used for enhanced cytopathic killing and/or to damp out further viral replication by killing cells exhibiting a replicative phenotype.

A preferred embodiment is an HSV tk gene cassette (Zjilstra et al. (1989) Nature 342:435; Mansour et al. (1988) Nature 336: 348; Johnson et al. (1989) Science 245: 1234: Adair et al. (1989) Proc. Natl. Acad. Sci (U.S.A.) 86: 4574; Capecchi, M. (1989) Science 244:1288, incorporated herein by reference) operably linked to the E2 promoter of Ad5 NT dl 1110 or an alternative promoter and/or enhancer (e.g., major late promoter, E1a promoter/enhancer, E1b promoter/enhancer), with a polydenylation site to form a tk expression cassette. The tk expression cassette (or other negative selection expression cassette) is inserted into the adenoviral genome, for example, as a replacement for a substantial deletion of the E3 gene.

Another negative selection gene that may be favorably used with the invention virions is cytosine deaminase. It is described in U.S. Pat. No. 5,358,866, which is incorporated herein by reference.

Diagnostic and In Vitro Uses

The replication deficient adenoviruses of the invention may be used to detect the presence of cells that are p53+, but lacking in p53 function.

A particularly noteworthy diagnostic application of the instant invention is applying E1b mutant virions to the treatment of neoplastic cells that exhibit normal levels of wild-type p53, but lack mismatch repair enzymantic activity. Thus, if a patient's tumor exhibits normal p53 levels, it is likely that the ablatic effect of the virus is due to the lack of mismatch repair activity. This finding could then be used to guide a physician to recommend the best course of treatment for the patient.

The genetic status of p53, normal or mutant, can be determined using known sequencing techniques, or as described in U.S. Pat. No. 5,362,623 or EPA 518 650. These references describe a method for detecting p53 in cellular extracts using DNA sequences that are specific for p53 binding.

Further mismatch repair activity can be assayed as described by Hawn, M. T., et al., Cancer Research vol. 55, pages 3721–3725 (1995).

Alternative diagnostic uses and variations are apparent; for example, a reporter gene (e.g., luciferase, b-galactosidase) may be substituted for a negative selection gene in a replication deficient adenovirus; transformed cells may be scored (such as in a cellular sample or transformation assay) by the expression of the reporter gene, which is correlated with expression of a replication phenotype indicating a lack of p53 and/or RB in a cell.

Therapeutic Methods

Therapy of neoplastic disease may be afforded by administering to a patient a composition comprising replication defective adenoviruses of the invention, including: replication deficient adenoviruses. E1b-p53$^{(-)}$ replication deficient adenoviruses, E1a/E1b double mutants, and replication deficient adenoviruses further comprising a negative selection gene. Typically a physician would biopsy a patient's tumor to determine its p53 and mismatch repair status. The preferred assay would be immunohistochemistry to reveal the presence of subpopulations of p53+ or p53– cells.

Human neoplasms comprising cells that exhibit p53 but lack p53 function based on the lack or substantial loss of mismatch repair activity may be treated with the replication deficient adenoviral constructs of the invention. For example, but not by way of limitation, a human patient or nonhuman mammal having a bronchogenic carcinoma, nasopharyngeal carcinoma, laryngeal carcinoma, small cell and non-small cell lung carcinoma, lung adenocarcinoma, hepatocarcinoma, pancreatic carcinoma, bladder carcinoma, colon carcinoma, breast carcinoma, cervical carcinoma, ovarian carcinoma, or lymphocytic leukemias may be treated by administering an effective antineoplastic dosage of an appropriate replication deficient adenovirus. Suspensions of infectious adenovirus particles may be applied to neoplastic tissue by various routes, including intravenous, intraperitoneal, intramuscular, subdermal, and topical. A adenovirus suspension containing about $10^3$ to $10^{13}$ or more virion particles per ml may be inhaled as a mist (e.g., for pulmonary delivery to treat bronchogenic carcinoma, small-cell lung carcinoma, non-small cell lung carcinoma, lung adenocarcinoma, or laryngeal cancer) or swabbed directly on a tumor site for treating a tumor (e.g., bronchogenic carcinoma, nasopharyngeal carcinoma, laryngeal carcinoma, cervical carcinoma) or may be administered by infusion (e.g., into the peritoneal cavity for treating ovarian cancer, into the portal vein for treating hepatocarcinoma or liver metastases from other non-hepatic primary tumors) or other suitable route, including direct injection into a tumor mass (e.g., a breast tumor), enema (e.g., colon cancer), or catheter (e.g., bladder cancer).

Antineoplastic replication deficient adenovirus mutants may be formulated for therapeutic and diagnostic administration to a patient having a neoplastic disease. For therapeutic or prophylactic uses, a sterile composition containing a pharmacologically effective dosage of one or more species of antineoplastic replication deficient adenovirus mutant is administered to a human patient or veterinary non-human patient for treatment of a neoplastic condition. Generally, the composition will comprise about $10^3$ to or more adenovirus particles in an aqueous suspension. A pharmaceutically acceptable carrier or excipient is often employed in such sterile compositions. A variety of aqueous solutions can be used, e.g., water, buffered water, 0.4% saline, 0.3% glycine and the like. These solutions are sterile and generally free of particulate matter other than the desired adenoviral virions. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. Excipients which enhance infection of cells by adenovirus may be included.

Replication deficient viruses may be delivered to neoplastic cells by liposome or immunoliposome delivery; such delivery may be selectively targeted to neoplastic cells on the basis of a cell surface property present on the neoplastic cell population (e.g., the presence of a cell surface protein which binds an immunoglobulin in an immunoliposome). Typically, an aqueous suspension containing the virions are encapsulated in liposomes or immunoliposomes. For example, a suspension of replication deficient adenovirus virions can be encapsulated in micelles to form immunoliposomes by conventional methods (U.S. Pat. No. 5,043,164, U.S. Pat. No. 4,957,735, U.S. Pat. No. 4,925,661; Connor and Huang (1985) *J. Cell Biol.* 101: 582; Lasic DD (1992) *Nature* 355: 279; *Novel Drug Delivery* (eds. Prescott L F and Nimmo W S: Wiley, New York, 1989); Reddy et al. (1992) *J. Immunol.* 148: 1585; incorporated herein by reference). Immunoliposomes comprising an antibody that binds specifically to a cancer cell antigen (e.g., CALLA, CEA) present on the cancer cells of the individual may be used to target virions to those cells.

The compositions containing the present antineoplastic replication deficient adenoviruses or cocktails thereof can be administered for prophylactic and/or therapeutic treatments of neoplastic disease. In therapeutic application, compositions are administered to a patient already affected by the particular neoplastic disease, in an amount sufficient to cure or at least partially arrest the condition and its complications. An amount adequate to accomplish this is defined as a "therapeutically effective dose" or "efficacious dose." Amounts effective for this use will depend upon the severity of the condition, the general state of the patient, and the route of administration.

In prophylactic applications, compositions containing the antineoplastic replication deficient adenoviruses or cocktails thereof are administered to a patient not presently in a neoplastic disease state to enhance the patient's resistance to recurrence of a neoplasm or to prolong remission time. Such an amount is defined to be a "prophylactically effective dose." In this use, the precise amounts again depend upon the patient's state of health and general level of immunity.

Single or multiple administrations of the compositions can be carried out with dose levels and pattern being selected by the treating physician. In any event, the pharmaceutical formulations should provide a quantity of the antineoplastic replication deficient adenoviruses of this invention sufficient to effectively treat the patient.

Antineoplastic replication deficient adenoviral therapy of the present invention may be combined with other antineoplastic protocols, such as conventional chemotherapy.
Propagation of Mutant Adenovirus Adenoviral mutants of the invention (e.g., replication deficient adenoviruses, E1b-p53$^{(-)}$ replication deficient adenoviruses) typically are propagated as viral stocks in a cell line (e.g., the 293 cell line ATCC # CRL 1573, American Type Culture Collection, Rockville, Md.; Graham et al. (1977) *J. Gen. Virol.* 36: 59) which can provide E1a function, E1b function, or both E1a and E1b functions, respectively, in trans to support replication and formation of infectious mutant virions.

The following examples are offered by way of example and not by way of limitation. Variations and alternate embodiments will be apparent to those of skill in the art.

EXPERIMENTAL EXAMPLE 1

Experiments were conducted to show that replication-deficient recombinant adenovirus mutants can be used to selectively kill neoplastic cells that exhibit normal levels of p53 when the cells lack, or are deficient in mismatch repair enzymatic activity.

The colon carcinoma cell line, HCT 116 was utilized. This cell line is known to be defective for mismatch repair activity, and is p53 positive. See, Anthoney, D. A., et al. Cancer Research, vol. 56, pages 1374–1381, (1996): and Drummond, J. T., et al. Journal of Biological Chemistry, vol. 271, pages 19645–19648 (1996). Two additional cell lines, derivatives of HCT 116, were also utilized: HCT 116 chr. 3 which is mismatch repair positive (MMR+), and HCT 116 chr. 3 rev. which is mismatch repair negative (MMR−). The former was produced by the transfer of a single normal human chromosome into HCT 116. Koi, M., et al. Cancer Research, vol. 54, pages 4308–4312 (1994). HCT 116 chr. 3 rev. (MMR−) was produced by selection of HCT 116 chr. 3 (MMR+) with N-methyl-N'-nitro-N-nitrosoguanidine. See, Hawn, M. T., et al. Cancer Research vol. 55, pages 3721–3725 (1995).

In order to determine the relationship of mismatch repair to adenovirus replication and cytopathogenicity in the HCT 116 cell lines the cell lines were infected with either wt adenovirus or the replication-deficient recombinant adenovirus mutant, dl 1520. As described above, this virus is E1b-. Burk, A., and Barker, J. Virology, vol. 156, pages 107–121 (1987).

The experiments were conducted as described in U.S. Pat. No. 5,677,178. See, also: Heise, C., et al. Nature Medicine, vol. 3, pages 639–645 (1997) and Bischoff, J. R., et al., Science, vol. 274, pages 373–376 (1996). The first experiment consisted of determining the cytopathogenicity of dl1520 or wild-type adenovirus to the different cell lines. Briefly, dl1520, or wild-type virus were added to the cells at m.o.i.s of 1, 0.1, or 0.01. A control without virus was also run. Cytopathic effect assays were carried out on cells at 70–90% confluence. Cells were infected for 90 minutes at increasing moi. Four to five days after infection the plates were stained with crystal violet to reveal the extent of cell destruction.

Figure 1:
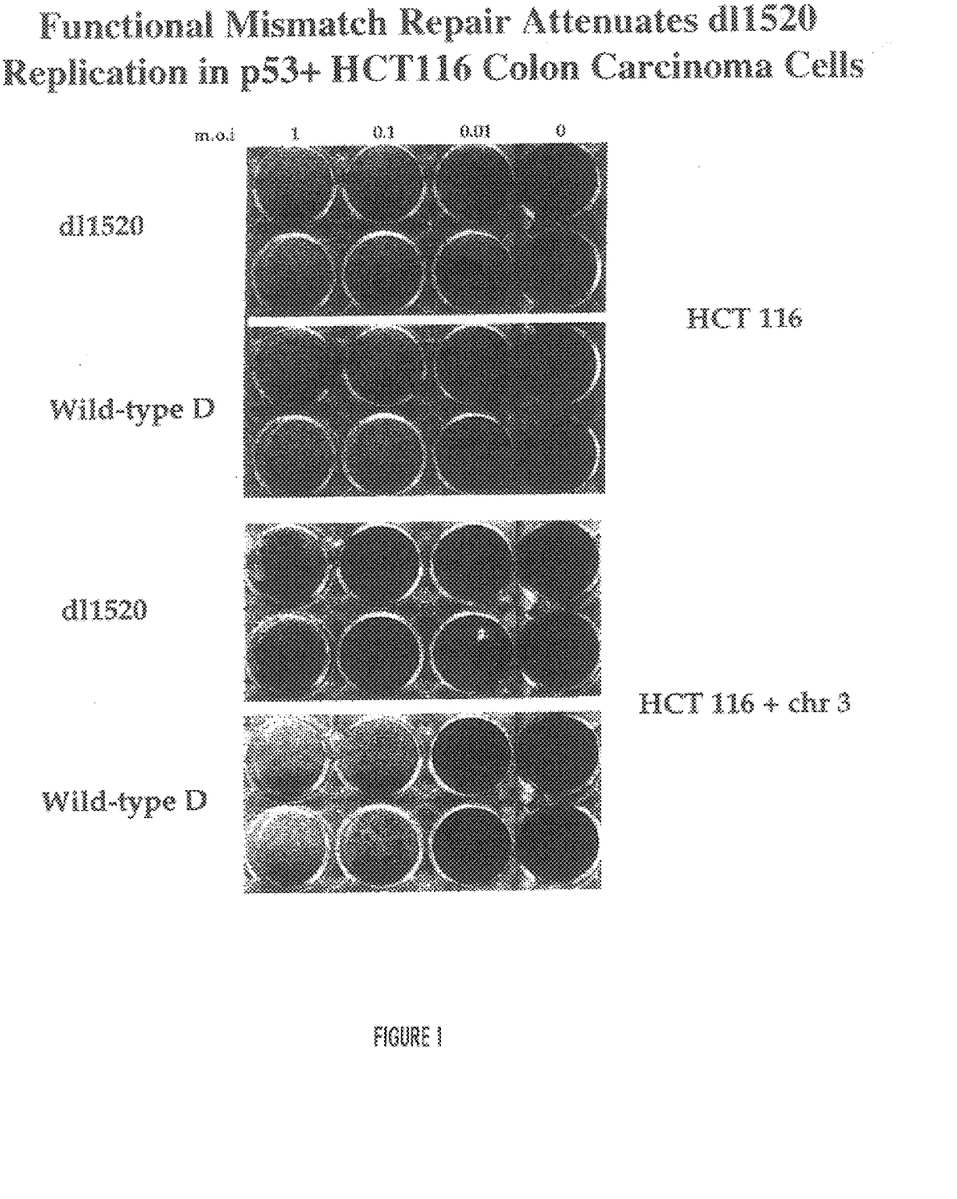
FIG. 1 shows the cytopathic effects of dl1520 or wild-type adenovirus at different moi on the p53+ cell lines HCT 116 (MMR-), and HCT 116 +chr3 (MMR+).

The results established that the cytopathogenicity of dl1520 correlates with the mismatch repair (MMR−) phenotype in the H 116 cell lines. Specifically, dl1520 showed significant lysis of H 116, which is MMR− and p53+, at a moi of 1, 0.1 and 0.01. When tested against HCT 116+chr3, which is MMR+ and p53+, dl1520 showed a small amount of lysis at a moi of 1, and little or no lysis at a moi of 0.1 or 0.01. Wild-type adenovirus was equally effective against both cell lines, showing extensive lysis at a moi of 1, 0.1, but little or no lysis at 0.01. The results are shown in FIG. 4. It was also observed that dl1520 effectively lysed the reverant cell line, HCT 116 chr3. rev. at a moi of 1 and 0.1 but not at 0.01. This line has lost chromosome 3, and is MMR−. It is also p53+, and thus shows similar lysis sensitivity to wild-type adenovirus as do HCT 116, and HCT 116+chr3.

Based on theses results, it is reasonable to conclude that the cytopathogenicity of wild-type adenovirus is independent of the mismatch repair phenotype status of the cell lines tested, whereas for the E1b mutant virus, dl1520, its capacity to lysis the cell lines correlates with their mismatch repair status.

As a measure of the ability of a E1b mutant adenovirus to replicate in neoplastic cells that are p53+ and that are mismatch repair deficient, the above HCT cell lines were infected with either dl1520 or wild-type adenovirus, and virus production determined by plaque assay. Briefly, forty eight hours after infection with either dl1520 or wild-type adenovirus at a moi of 1 or 10, cells were scraped into cell culture media and frozen. Lysates were prepared by three cycles of freezing and thawing, followed by a 30 second pulse in a sonicator water bath. Serial dilutions of the lysates were titered on HEK293 cell.

Figure 2:
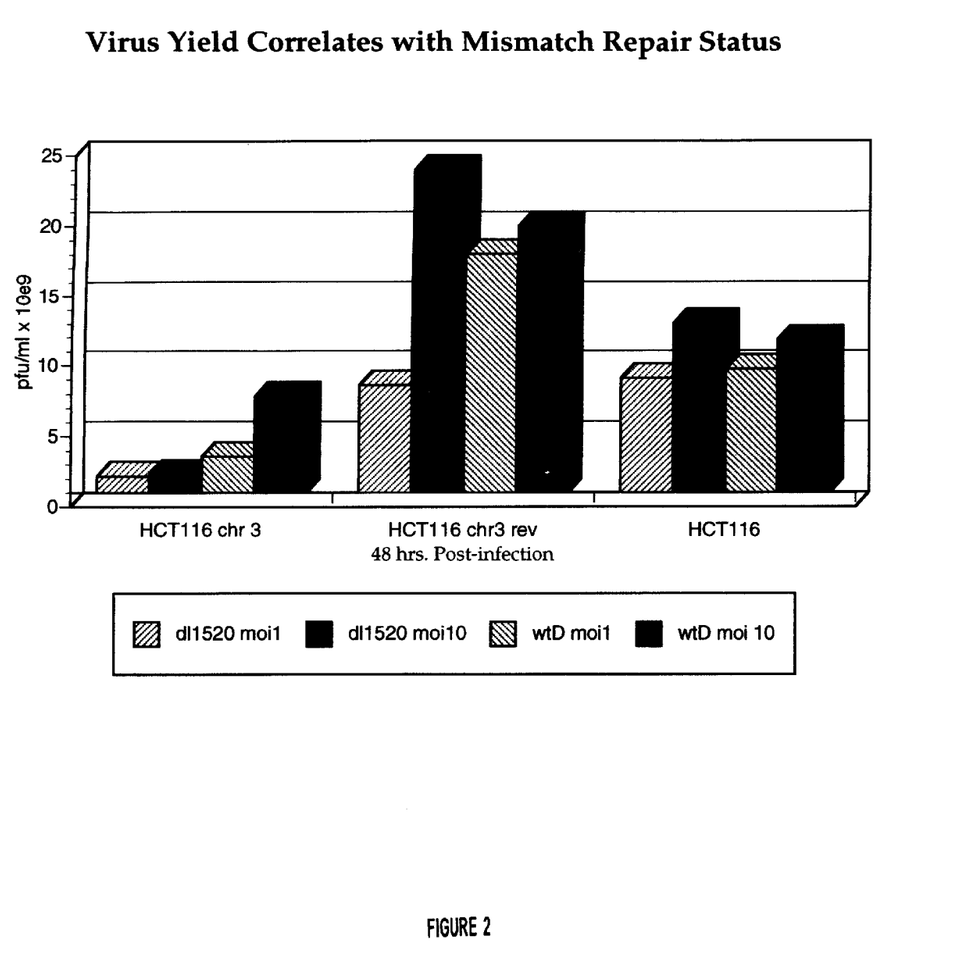
FIG. 2 shows the pfu produced by the cell lines HCT 116 (MMR-), HCT 116 +chr3 (MMR+), and HCT 116 +chr3 rev.(MMR-) after infection at different moi with either dl1520 or wild-type adenovirus.

FIG. 2 shows the results. It is apparent for HCT 116 cells that at the same moi, 1 or 10, the pfu are similar for both dl1520 and wild-type virus. However, for the cell line HCT 116 chr3 (MMR+), the pfu are considerably greater for wild-type adenovirus than for dl1520 at both moi. This finding is consistent with the postulate that in p53+ cells the absence of mismatch repair facilitates E1b mutant effects. This is further borne out with experiments on HCT 116 chr3 rev. (MMR−). Here both wild-type adenovirus and dl1520 exhibited similar pfu at a moi of either 1 or 10.

Although the present invention has been described in some detail by way of illustration for purposes of clarity of understanding, it will be apparent that certain changes and modifications may be practiced within the scope of the claims.

What is claimed is:

1. A method for ablating neoplastic cells in a cell population, comprising the steps of:

contacting under infective conditions (1) a recombinant replication deficient adenovirus lacking an expressed viral oncoprotein capable of binding a functional p53 tumor suppressor gene product, with (2) a cell population comprising non-neoplastic cells containing said functional tumor suppressor gene product capable of forming a bound complex with a viral oncoprotein, and neoplastic cells containing said functional tumor suppressor gene product and said neoplastic cells are deficient in or lack mismatch repair activity, thereby generating an infected cell population and ablating said neoplastic cells.

2. A method according to claim 1, wherein the viral oncoprotein is an adenovirus E1b polypeptide.

3. A method according to claim 1, wherein the neoplastic cells are p53$^{(+)}$.

4. A method according to claim 1, wherein the recombinant replication deficient adenovirus is dl1520.

5. A method according to claim 1, wherein said cell population comprising neoplastic cells and non-neoplastic cells is present in a mammal and said contacting step is performed in vivo by administering the recombinant replication deficient adenovirus to an individual.

6. A method according to claim 1, wherein the recombinant replication deficient adenovirus is an E1a/E1b double mutant.

7. A method according to claim 3, wherein the recombinant replication deficient adenovirus does not encode an E1a polypeptide capable of binding RB and also does not encode a E1b p55 polypeptide capable of binding p53.

8. A method according to claim 5, wherein the mammal is a human.

9. A method for diagnosing the susceptibility of a patient's tumor to treatment with recombinant adenovirus, said tumor comprising neoplastic cells that exhibit the tumor suppressor p53, and said recombinant adenovirus having the property of lacking an expressed viral oncoprotein capable of binding a functional p53 tumor suppressor gene product; comprising assaying said neoplastic cells for mismatch repair activity, and determining if said neoplastic cells are deficient in, or lack, said mismatch repair activity and if said neoplastic cells are deficient in, or lack mismatch repair activity diagnosing said cells as susceptible to treatment with said recombinant adenovirus.

10. A method according to claim 9, wherein the recombinant replication deficient adenovirus is an E1b mutant.

11. A method according to claim 9 wherein said mismatch repair activity is assayed enzymatically.

12. A method according to claim 10, wherein the recombinant replication deficient adenovirus is Ad5 dl1520.

* * * * *